US00PP22456P2

(12) United States Plant Patent
Klinkhamer

(10) Patent No.: US PP22,456 P2
(45) Date of Patent: Jan. 10, 2012

(54) ***GERANIUM* PLANT NAMED 'MIDNIGHT CLOUDS'**

(50) Latin Name: ***Geranium* hybrid**
Varietal Denomination: Midnight Clouds

(76) Inventor: Lucas Klinkhamer, Hillegom (NL)

( * ) Notice: Subject to any disclaimer, the term of this patent is extended or adjusted under 35 U.S.C. 154(b) by 0 days.

(21) Appl. No.: 12/807,266

(22) Filed: Sep. 1, 2010

(51) Int. Cl.
*A01H 5/00* (2006.01)
(52) U.S. Cl. ..... Plt./324
(58) Field of Classification Search ..... Plt./324
See application file for complete search history.

*Primary Examiner* — Susan McCormick Ewoldt
(74) *Attorney, Agent, or Firm* — Penny J. Aguirre

(57) ABSTRACT

A new cultivar of *Geranium*, 'Midnight Clouds', characterized by its large, sturdy, dark purple-green leaves, its white-light pink flowers held on sturdy red stems, its long blooming season, and its resistance to powdery mildew.

2 Drawing Sheets

Botanical classification: *Geranium* hybrid.
Cultivar designation: 'Midnight Clouds'.

BACKGROUND OF THE INVENTION

The present invention relates to a new and distinct cultivar of *Geranium* plant, botanically of hybrid origin and known as *Geranium* 'Midnight Clouds' and will be referred to hereafter by its cultivar name, 'Midnight Clouds'.

The inventor discovered the new cultivar, 'Midnight Clouds', a naturally occurring whole plant mutation in his garden in Hillegom, The Netherlands in June of 2008. The parentage of 'Midnight Clouds' is unknown, however it is likely to be a hybrid between *Geranium pratense* and *Geranium maculatum* based on its characteristics and their proximity in the garden in which 'Midnight Clouds' was discovered.

Asexual reproduction of the new cultivar was first accomplished by tissue culture under the direction of the Inventor in Rijswijk, The Netherlands in 2009. Propagation has determined that the characteristics of this cultivar are stable and are reproduced true to type in successive generations.

SUMMARY OF THE INVENTION

The following traits have been repeatedly observed and represent the characteristics of 'Midnight Clouds'. These attributes in combination distinguish 'Midnight Clouds' as a new and distinct cultivar of *Geranium*.

1. 'Midnight Clouds' exhibits foliage that is dark purple-green in color.
2. 'Midnight Clouds' exhibits leaves that are large and sturdy.
3. 'Midnight Clouds' exhibits white-light pink flowers held on sturdy red stems.
4. 'Midnight Clouds' exhibits a long blooming season; blooming from May to September in The Netherlands.
5. 'Midnight Clouds' has been observed to be resistant to powdery mildew.

'Midnight Clouds' differs from cultivars of its likely parent species in having larger and stronger leaves. 'Midnight Clouds' can be most closely compared to 'Midnight Reiter' (not patented). 'Midnight Clouds' differs from 'Midnight Reiter' in having larger and stronger leaves, in having greater resistance to powdery mildew and in having white-light pink flowers rather than lavender-blue. 'Midnight Clouds' can also be compared to 'Hocus Pocus' (not patented). 'Hocus Pocus' differs from 'Midnight Clouds' in having a more compact mounded plant habit and in having light purple flowers.

BRIEF DESCRIPTION OF THE DRAWING

The accompanying colored photographs illustrate the overall appearance and distinct characteristics of the new *Geranium*. The photographs were taken of a one year-old plant of 'Midnight Clouds' as grown outdoors in a one-gallon container in Noordwijk, The Netherlands.

The photograph in FIG. 1 is a view of a plant of 'Midnight Clouds' in bloom.

Figure 1:
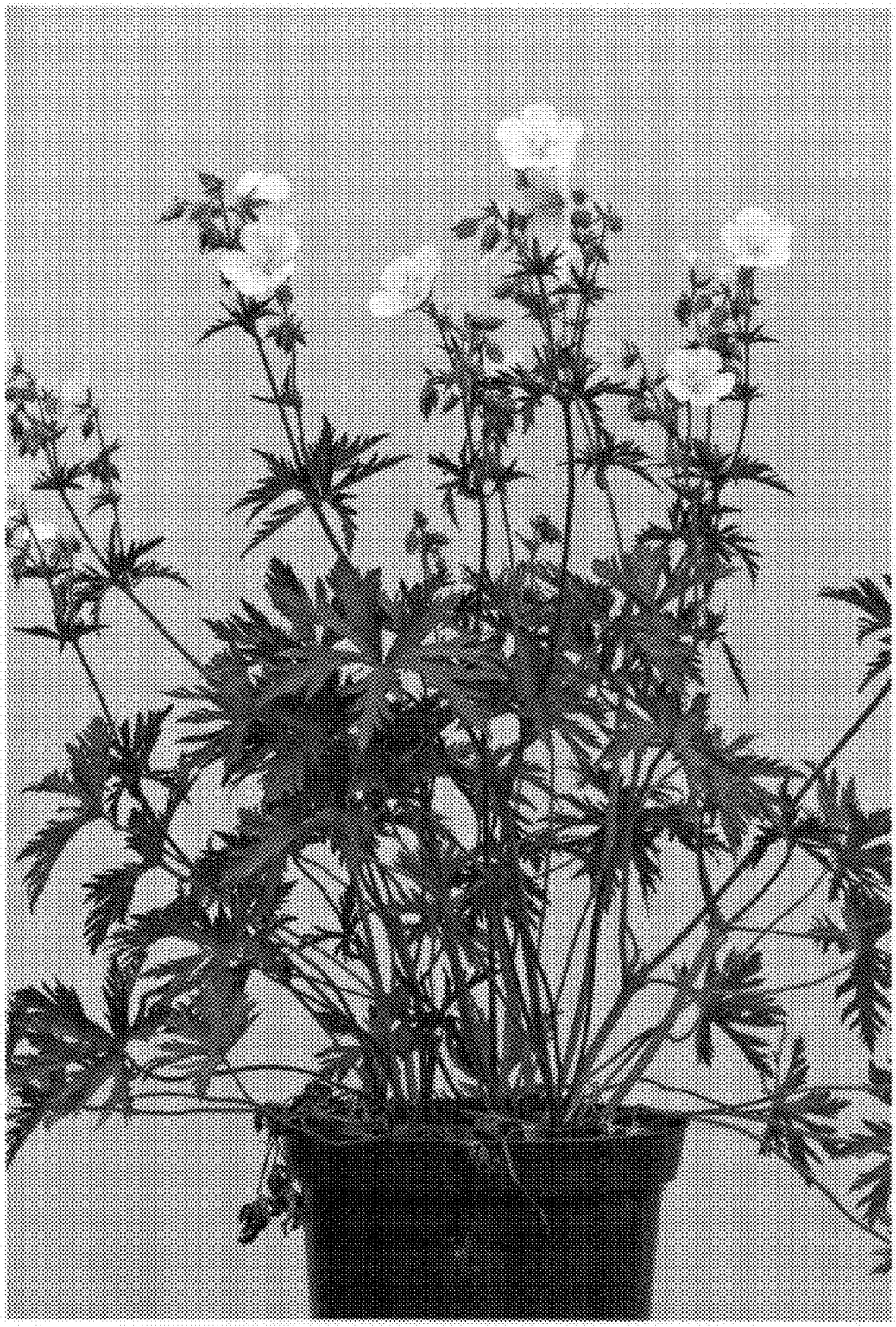
Figure 2:
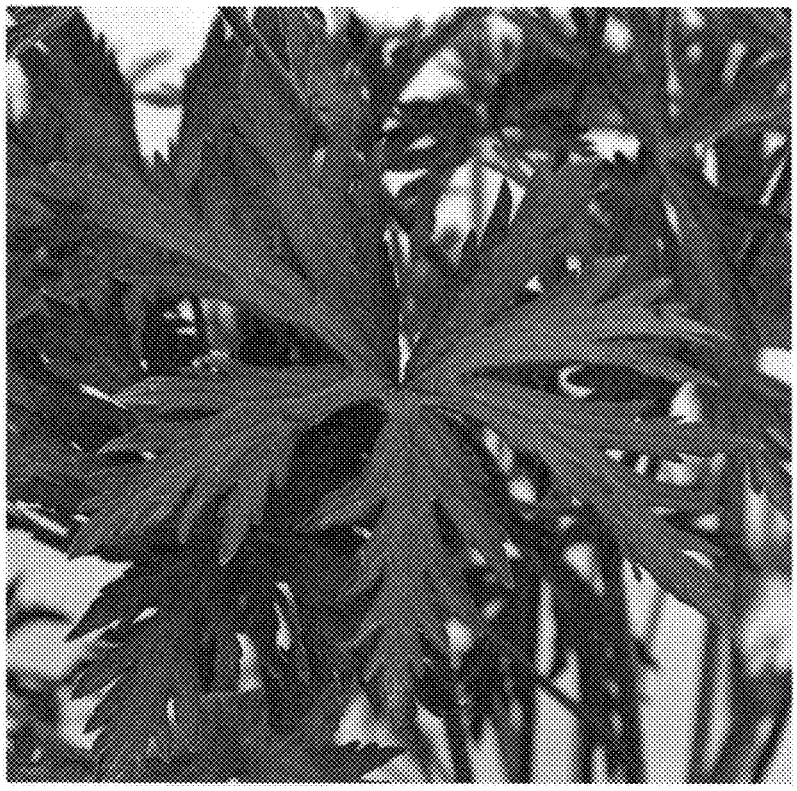
Figure 3:
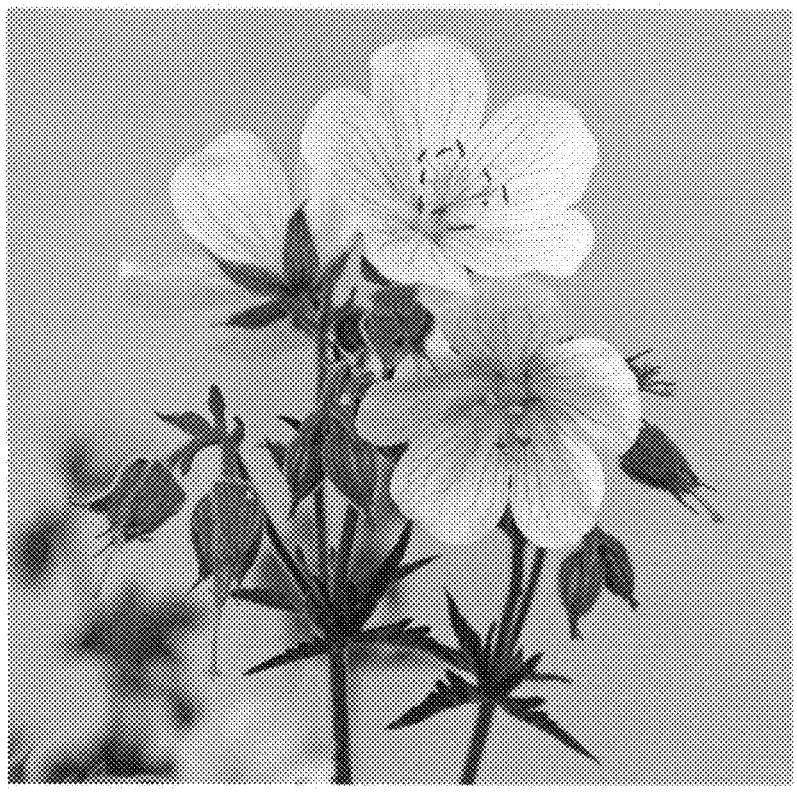

The photograph in FIG. 2 is of a close-up view of a leaf of 'Midnight Clouds' while the photograph in FIG. 3 provides a close-up view of the flowers of close-up view of 'Midnight Clouds'. The colors in the photographs are as close as possible with the digital photography and printing techniques utilized and the color codes in the detailed botanical description more accurately describe the colors of the new *Geranium*.

DETAILED BOTANICAL DESCRIPTION OF THE PLANT

The following is a detailed description of one year-old plants of the new cultivar as field-grown in Noordwjik, The Netherlands, with day temperatures ranging between 12° and 23° C. and average night temperatures between 5° and 17° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period.*—May to September in The Netherlands.

*Plant habit.*—Herbaceous perennial with broadly upright spreading growth habit.

*Height and spread.*—Average of 47.4 cm in height and about 48.1 cm in spread.

*Cold hardiness.*—At least to U.S.D.A. Zone 5.

*Heat tolerance.*—At least tolerant to temperature up to 35° C.

*Diseases and pests.*—Resistance to powdery mildew has been observed.

*Root description.*—Fibrous roots extending from stout rootstock.

*Branching habit.*—Moderately branched with an average 12 basal and lateral branches on a one year-old plant.

Growth and propagation:

*Growth rate.*—Moderate, growth rate in stems is about 12 cm per month.

*Propagation.*—Tissue culture.

*Time required from root initiation to finishing.*—20 weeks in 9 cm containers or larger.

Stem description:

*Stem size.*—Average of 15.9 cm in length and 4 mm in width, lateral branches average of 28.5 cm in length, 3 mm in diameter.

*Stem shape.*—Round.

*Stem color.*—183B.

*Stem surface.*—Glossy, densely pubescent with soft hairs 0.3 mm in length, approximately NN155D in color.

*Stem strength.*—Moderately strong.

*Internode length.*—Average of 11.7 cm, ranging from 3.4 to 18.5 cm in length.

Foliage description:

*Leaf shape.*—Orbicular, palmately cleft with an average of 7 lobes.

*Leaf division.*—Simple.

*Leaf base.*—Hastate.

*Leaf apex.*—Acute.

*Leaf venation.*—Palmate, upper surface 147A in color, lower surface 148B.

*Leaf margins.*—Palmately cleft, lobes deeply serrate.

*Leaf attachment.*—Petiolate.

*Leaf arrangement.*—Opposite.

*Leaf surface.*—Upper surface; dull, pubescent, lower surface; sparsely pubescent on main and secondary veins, hairs 0.3 mm in length, approximately 157D in color.

*Leaf color.*—Upper surface; emerging 147A margins strongly suffused with a blend of N186B and 200A, mature 147A margins strongly suffused with a blend of N186C and 200B, lower surface; emerging 147B margins strongly suffused with a blend of N186C and 200C, mature a blend of 138A and 147B margins slightly suffused with N186C.

*Leaf size.*—Average of 8.8 cm in length and 10.5 cm in width.

*Leaf quantity.*—Average of 6 (3 pairs) per lateral branch.

*Petioles.*—An average of 14.7 cm in length and 2 mm in width, color a blend of 178A and 178B, pubescent surface.

*Stipules.*—Two at each leaf base, lanceolate in shape, average of 1.8 cm in length and 3 mm in width, upper and lower surface N199C, pubescent surface on upper and lower surface.

*Durability of foliage to stress.*—High, leaves are thick and sturdy.

Flower description:

*Inflorescence type.*—Single, rotate, arranged in pairs.

*Inflorescence size.*—Average of 5.2 cm in height, 4.3 cm in width.

*Lastingness of flowers.*—About 7 days, self cleaning.

*Flower size.*—Average of 1.3 cm in depth and 4.0 cm in diameter.

*Flower fragrance.*—None.

*Flower number.*—Average of 3 open flowers and 11 buds per lateral branch, about 170 buds and flowers per plant, with 15% open at any stage.

*Flower aspect.*—Outward to slightly upright.

*Flower bud size.*—Average of 1.1 cm in length, 5 mm in width.

*Flower bud color.*—148B, with stripes darker than 177A.

*Flower bud surface.*—Densely covered with short glandular hairs 0.5 mm, 156D in color.

*Flower bud shape.*—Elliptic.

*Petals.*—5, un-fused and arranged in a rotate form, obcordate in shape, entire margins, rounded apex, an average of 2.2 cm in length and 1.6 cm in width, color: upper surface opening and fully opened; a color between 76D and NN155D, base N155D, veins a blend of 70C and 70D, lower surface opening and fully opened; a color between 76D and NN155D, base; when opening between 76D and NN155D, base N155D, veins a blend of 72C and 72D, upper and lower surface fading to between 76D and NN155D, veins 77C, surface: smooth, velvety, sparsely covered with hairs 0.3 mm in length, a blend of 75C and 75D in color.

*Calyx.*—Rotate, cupped.

*Sepals.*—Average of 5, ovate to narrowly ovate, entire margins, mucronate apex, cuneate base, an average of 1.3 cm length, 4.5 mm in width, surface dull and glabrous, color: immature and mature upper surface; a blend of 146A and 146B, center suffused with colors ranging from 152A and 152B to 180B and 180C, immature lower surface; 148B with stripes darker than 177A, mature lower surface; 177A with stripes 200B in color.

*Peduncles.*—Round in shape, an average of 2.1 cm in length and 1.5 mm in diameter, 178A in color, held at about a 25° angle relative to lateral branch.

*Pedicels size.*—Round in shape, an average of 0.8 cm in length and 1 mm in width, 178A in color, lateral flowers are held at about 50° relative to peduncle.

Reproductive organs:

*Gynoecium.*—1 pistil, about 1.0 cm in length, stigmas; 5, decurrent, and 151B in color, style; about 8 mm in length and a blend of 151B and 151C in color, ovary; 143C in color.

*Androcoecium.*—10 stamens, anthers; dorsifixed, oblong in shape, 2 mm in length, 0.5 mm in width, and a blend of 182A an 186A in color, filaments; 8 mm in length and a blend of 186B and 186C in color, pollen; moderate in abundance and a blend of 12A and 13B in color.

*Fruit.*—Schizocarp, average of 14 per lateral branch, 170 per plant, 3.6 cm in length, 0.6 cm in diameter, a blend of 146A and 146C in color, surface softly pubescent with glandular hairs 0.75 mm in length and a blend of NN155C and NN155D in color.

*Seed.*—Average of 5 seeds per fruit, 3 mm in length, 2 mm in diameter, 200A in color.

It is claimed:

1. A new and distinct cultivar of *Geranium* plant named 'Midnight Clouds' as herein illustrated and described.

* * * * *